(12) United States Patent
Oleson et al.

(10) Patent No.: US 11,229,399 B2
(45) Date of Patent: *Jan. 25, 2022

(54) SYSTEM AND METHOD FOR MONITORING EFFICIENCY VERSUS FATIGUE

(71) Applicant: Under Armour, Inc., Baltimore, MD (US)

(72) Inventors: Mark A. Oleson, Baltimore, MD (US); F. Grant Kovach, Baltimore, MD (US); Nathan Dau, Baltimore, MD (US); Angela Nelligan, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 143 days.

This patent is subject to a terminal disclaimer.

(21) Appl. No.: 16/274,972

(22) Filed: Feb. 13, 2019

(65) Prior Publication Data

US 2019/0175102 A1 Jun. 13, 2019

Related U.S. Application Data

(63) Continuation of application No. 15/082,402, filed on Mar. 28, 2016, now Pat. No. 10,251,596.

(51) Int. Cl.
*A61B 5/02* (2006.01)
*A61B 5/00* (2006.01)
(Continued)

(52) U.S. Cl.
CPC .......... *A61B 5/486* (2013.01); *A61B 5/0205* (2013.01); *A61B 5/112* (2013.01); *A61B 5/02438* (2013.01);
(Continued)

(58) Field of Classification Search
CPC ....... A61B 5/486; A61B 5/0205; A61B 5/112; A61B 5/6898; A61B 2503/10; A61B 5/02438

See application file for complete search history.

(56) References Cited

U.S. PATENT DOCUMENTS 6,898,550 B1 5/2005 Blackadar
2014/0222173 A1 8/2014 Gledwoyn
(Continued)

*Primary Examiner* — Amanda K Hulbert
*Assistant Examiner* — Natasha Patel
(74) *Attorney, Agent, or Firm* — Maginot, Moore & Beck LLP

(57) ABSTRACT

A receiver apparatus is configured to receive a first and second signal from one or more sensors, the first signal comprising a measure of one or more exercise parameters of the user at a first time period of an exercise session, and the second signal comprising a measure of the one or more exercise parameters at a second time period. A processor is configured to store the first and second signals in a memory, generate a fatigue signal based on a comparison of the measured one or more exercise parameters of the first signal to the respective measured one or more exercise parameters of the second signal, generate an exercise efficiency signal based on a comparison of the measured one or more exercise parameters of the second signal to an a priori exercise parameter threshold, and cause the exercise efficiency signal and the fatigue signal to be simultaneously displayed.

21 Claims, 5 Drawing Sheets

(51) Int. Cl.
  *A61B 5/0205* (2006.01)
  *A61B 5/11* (2006.01)
  *A61B 5/024* (2006.01)

(52) U.S. Cl.
  CPC ......... *A61B 5/6898* (2013.01); *A61B 2503/10* (2013.01)

(56) References Cited

U.S. PATENT DOCUMENTS

| | | | | |
|---|---|---|---|---|
| 2015/0142329 | A1* | 5/2015 | Ostman | A61B 5/222 |
| | | | | 702/19 |
| 2015/0182130 | A1* | 7/2015 | Utter, II | A61B 5/681 |
| | | | | 600/483 |
| 2015/0223743 | A1* | 8/2015 | Pathangay | A61B 5/18 |
| | | | | 600/301 |
| 2016/0030804 | A1* | 2/2016 | Mizuochi | A61B 5/11 |
| | | | | 482/8 |
| 2016/0232807 | A1* | 8/2016 | Ghaffari | G09B 19/00 |
| 2017/0188894 | A1* | 7/2017 | Chang | G16H 50/30 |

* cited by examiner

SYSTEM AND METHOD FOR MONITORING EFFICIENCY VERSUS FATIGUE

CROSS-REFERENCE TO RELATED APPLICATIONS

This application is a continuation of U.S. patent application Ser. No. 15/082,402, filed Mar. 28, 2016, the entire contents of which are incorporated herein by reference.

BACKGROUND

The present invention generally relates to devices and methods generating fatigue and efficiency data based on input parameters.

There exists a need for a device and method to generate fatigue and efficiency data related to a user's activities.

BRIEF SUMMARY OF THE DRAWINGS

The accompanying drawings, which are incorporated in and form a part of the specification, illustrate example embodiments and, together with the description, serve to explain the principles of the invention. In the drawings.

DETAILED DESCRIPTION

Overview

Figure 1:
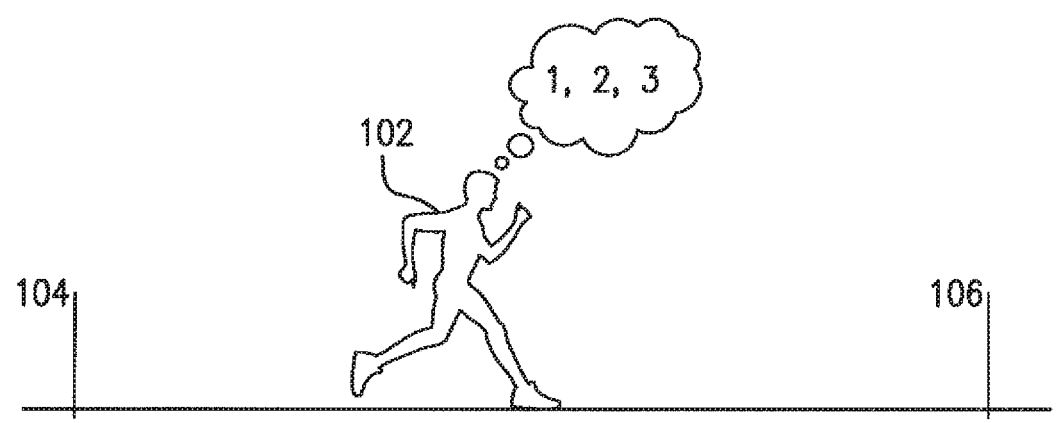
FIG. 1 illustrates a conventional method to determine a runner's speed and cadence.

An aspect of the present invention is drawn to a device for use by a user, the device comprising a receiver apparatus and a processor. The receiver apparatus is configured to receive a first signal and a second signal from one or more sensors, the first signal comprising a measure of one or more exercise parameters of the user at a first time period of an exercise session, and the second signal comprising a measure of the one or more exercise parameters of the user at a second time period of the exercise session. The processor is configured to store the first and second signals in a memory associated to the processor, generate a fatigue signal based on a comparison of the measured one or more exercise parameters of the first signal to the respective measured one or more exercise parameters of the second signal, generate an exercise efficiency signal based on a comparison of the measured one or more exercise parameters of the second signal to an a priori exercise parameter threshold, and cause the exercise efficiency signal and the fatigue signal to be simultaneously displayed on a display device.

Another aspect of the present invention is drawn to a method that includes receiving a first detected signal based on a first parameter detected at a first time, the first parameter comprising at least one of: a heartrate of the user, a cadence of the user, a speed of the user, and a loft of a foot of the user. The method further includes receiving a second detected signal based on a second parameter detected at a second time, the second parameter either (i) a different parameter than the first parameter and comprising at least one of: the heartrate of the user, the cadence of the user, the speed of the user, and the loft of the foot of the user, wherein the second parameter is detected at the first time, or (ii) a same parameter as the first parameter. Additionally, the method includes generating, via an efficiency generating component, an efficiency signal. When the second parameter is a same parameter as the first parameter, the efficiency signal is generated based on a comparison of the first detected signal to the second detected signal. When the second detected parameter is a different parameter than the first parameter, the efficiency signal is generated based on a comparison of the first detected signal and the second detected signal to respective predetermined thresholds therefor.

Another aspect of the present invention is drawn to non-transitory, tangible, computer-readable media having computer-readable instructions stored thereon, the computer-readable instructions being capable of being read by a computer and being capable of instructing the computer to receive a first sensed parameter of the user at a first time, the first sensed parameter selected from a first group of parameters for the user, and receive a second sensed parameter of the user at a second time, the second sensed parameter comprising at least (i) a different one of the first group or (ii) at least one of a second group. The method further includes generate an efficiency signal. The instructions being capable of instructing the computer to further generate a fatigue signal and display at least one of the efficiency signal and the fatigue signal. When the second sensed parameter comprises a member of the second group, the generation of the efficiency signal and/or the fatigue signal comprises a comparison of the first sensed parameter to the second sensed parameter. When the second sensed parameter comprises a member of the first group, the generation of the efficiency signal and/or the fatigue signal comprises a comparison of each of the first and second sensed parameters to respective thresholds therefor.

Example Embodiments

One of the recent trends in fitness is using a wearable device to record data related to the activity a user is performing. The data can be downloaded directly to a computer, smartphone, or other smart device, and the user can refer to the downloaded data to track his progress. A conventional wearable device may incorporate various sensors to determine activity levels. Non-limiting examples of such sensors include temperature sensors, pressure sensors, water sensors, moisture sensors, communication channel sensors, electric field sensors, current sensors, voltage sensors, impedance sensors, magnetic field sensors, accelerometers, altimeters, GPS sensors, magnetometers, optical sensors, and chemical sensors.

Traditionally, individuals that run for exercise are interested in understanding their speed, cadence, and loft during a run, and how to become a more efficient runner, even when fatigued. Speed is how fast the individual is running. Cadence is the rate at which the individual picks up, and puts down, his feet. Loft is how high the individual's foot lifts off the ground. A runner is also typically concerned with his heart rate during a run.

FIG. 1 illustrates a conventional method to determine a runner's speed and cadence.

As shown in the figure, runner 102 is running between two locations, starting location 104 and ending location 106. To determine his speed, runner 102 must know the distance between starting location 104 and ending location 106 before beginning the run, and he must also have a watch or some other timekeeping device to take note of the starting and ending time.

At the end of the run, runner 102 can determine his overall speed for the entire run by dividing the total distance from starting location 104 to ending location 106 by the total time elapsed. However, this only provides runner 102 an overall speed for the entire run and not his speed at a given point in time during the run or during instances where he is more or less fatigued. There exists a need for a device and method to provide a runner with more information regarding his speed at a given point.

To determine his cadence, runner 102 must count the number of steps he takes between two points, for example from starting location 104 to ending location 106, and he must know the amount of time during which he is counting steps. If runner 102 loses count, he must start over. In addition, even if runner 102 accurately determines his cadence for the run, this only provides him with his cadence for the entire run, not his cadence at a given point during the run, nor his cadence during instances where he is more or less fatigued. There exists a need for a device and method to provide a runner with more information regarding his cadence at a given point.

Devices and methods in accordance with aspects of the present invention to address these issues will now be discussed with reference to FIGS. 2-7.

Figure 2:
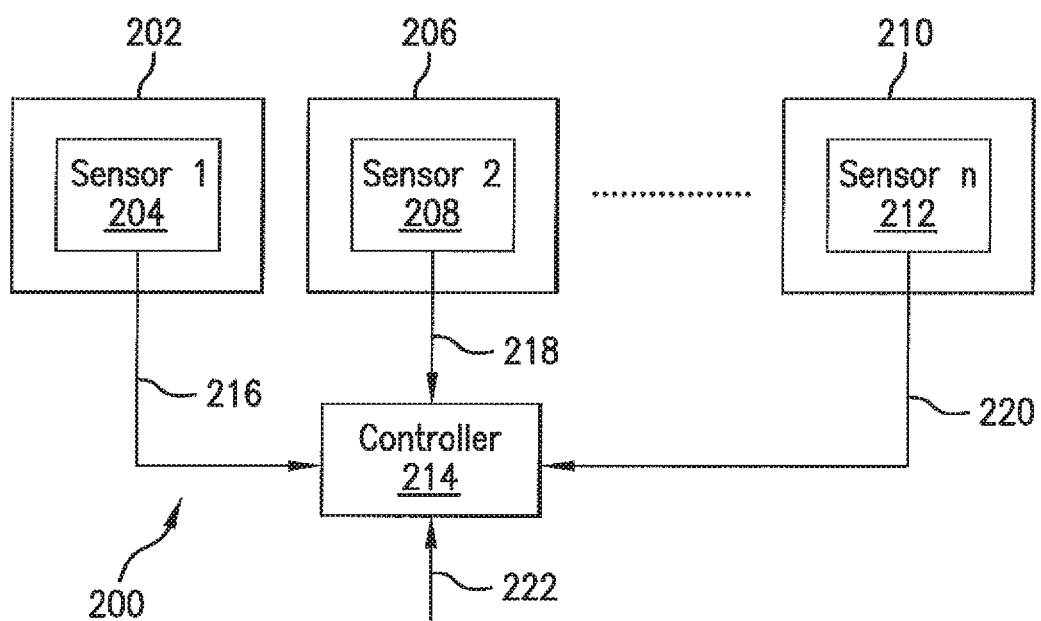
FIG. 2 illustrates a system of sensors in communication with a controller in accordance with aspects of the present invention.

FIG. 2 illustrates an example system of sensors in communication with a controller in accordance with aspects of the present invention.

As shown in the figure, system 200 includes a plurality of devices, a sample of which includes a device 202, a device 206, and device 210. System 200 additionally includes a plurality of sensors, a sample of which includes a sensor 204, a sensor 208 and sensor 212. System 200 still further includes a controller 214 and a plurality of communication channels, a sample of which includes communication channels 216, 218, 220 and 222.

In this example, device 202, device 206, device 210 and controller 214 are illustrated as individual devices. However, in some embodiments, at least two of device 202, device 206, device 210 and controller 214 may be combined as a unitary device.

Further, in some embodiments, at least one of device 202, device 206, device 210 and controller 214 may be implemented as a processor working in conjunction with a tangible processor-readable media for carrying or having processor-executable instructions or data structures stored thereon. Non-limiting examples of tangible processor-readable media include physical storage and/or memory media such as RAM, ROM, EEPROM, CD-ROM or other optical disk storage, magnetic disk storage or other magnetic storage devices, or any other medium which can be used to carry or store desired program code means in the form of processor-executable instructions or data structures and which can be accessed by special purpose computer. For information transferred or provided over a network or another communications connection (either hardwired, wireless, or a combination of hardwired or wireless) to a computer, the processor may properly view the connection as a processor-readable medium. Thus, any such connection may be properly termed a processor-readable medium. Combinations of the above should also be included within the scope of processor-readable media.

Communication channels 216, 218, 220 and 222 may be any known type of wired or wireless communication channel that enables communication between two devices.

Each of device 202, device 206, and device 210 may be any device that is capable of including a sensor for tracking activity, non-limiting examples of which include shoes, smartwatches, smartphones, clothing, eyewear, armbands and headbands. For purposes of discussion, this embodiment is described with three devices. However, it should be noted that in accordance with aspects of the present invention, any number of devices may be used, wherein each device is capable of tracking activity. Further, it should be noted that for each additional device, there will be a corresponding communication channel connecting such additional devices to controller 214.

For purposes of brevity, throughout this document device 202 is a pair of shoes, device 206 is a smartwatch, and device 210 is a smartphone.

Sensor 204, sensor 208 and sensor 212 may be any sensors that track a user's activity based on certain detected parameters, non-limiting examples of which include temperature sensors, pressure sensors, water sensors, moisture sensors, communication channel sensors, electric field sensors, current sensors, voltage sensors, impedance sensors, magnetic field sensors, accelerometers, altimeters, GPS sensors, magnetometers, optical sensors, and chemical sensors, and combinations thereof. Sensor 204, sensor 208 and sensor 212 communicate with controller 214 via communication channels 216, 218, and 220, respectively, to provide controller 214 with detected signals based on the detected parameters for further processing.

Controller 214 receives detected signals from sensors 204, 208, and 212, and further processes the signals, creating fatigue and efficiency signals. Controller 214 provides the fatigue and efficiency signals to the user via communication channel 222. Controller 214 is shown as being a separate component from devices 202, 206 and 210; however controller 214 may also be integrated into one of devices 202, 206 and 210. As a non-limiting example, controller 214 may be included as part of smartwatch 206, and shoes 202 and smartphone 210 would communicate with smartwatch 206 via controller 214 integrated within smartwatch 206.

The operation of controller 214 will be further described with reference to FIG. 3, and the operation of system 200 will be further described with reference to FIGS. 3-7.

Figure 3:
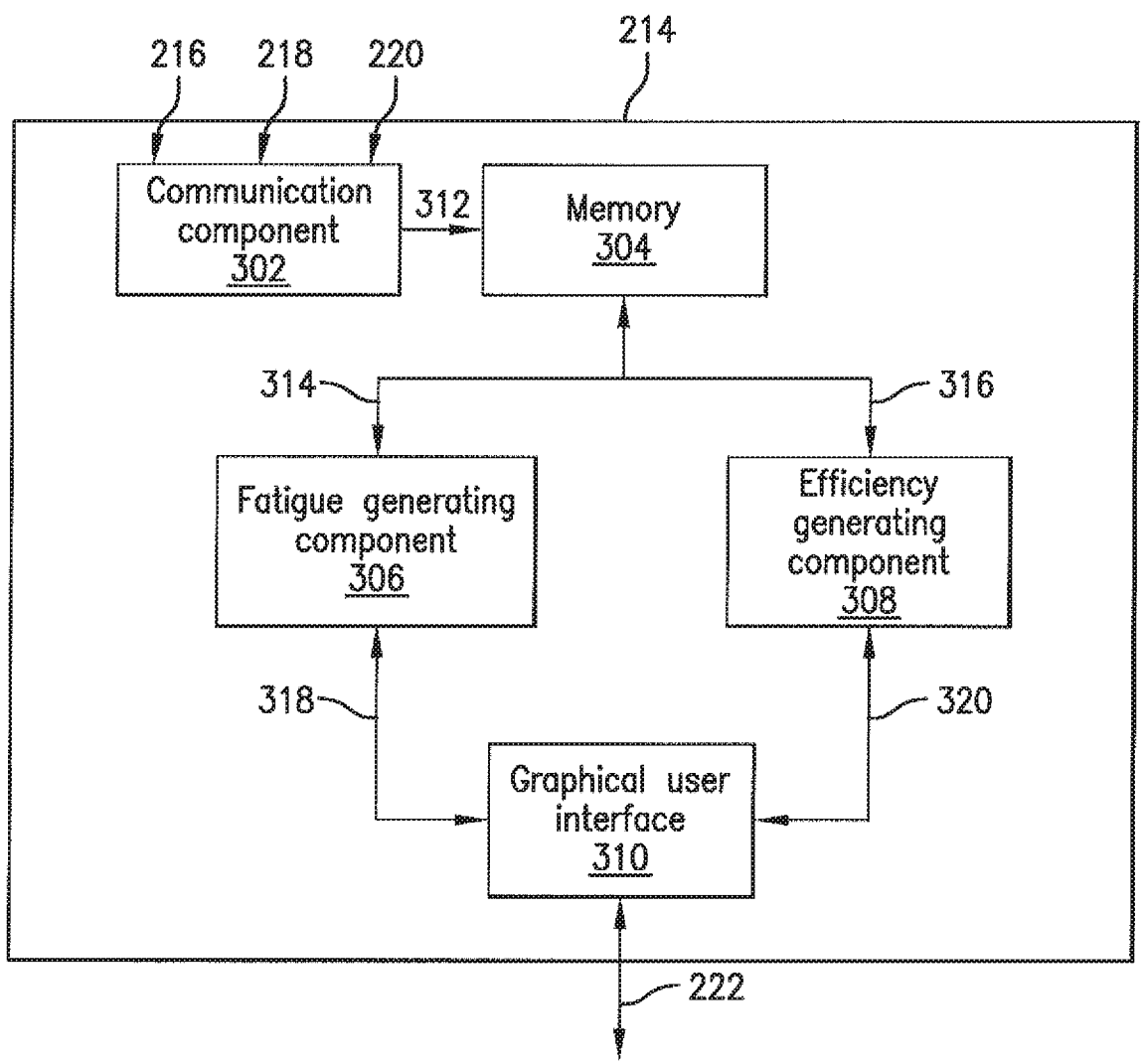
FIG. 3 illustrates a controller in accordance with aspects of the present invention.

FIG. 3 illustrates an example of controller 214 in accordance with aspects of the present invention.

As shown in the figure, controller 214 includes a communication component 302, a memory 304, a fatigue generating component 306, an efficiency generating component 308, a graphical user interface (GUI) 310, and communication channels 312, 314, 316, 318 and 320.

In this example, communication component 302, memory 304, fatigue generating component 306, efficiency generating component 308 and GUI 310 are illustrated as individual devices. However, in some embodiments, at least two of communication component 302, memory 304, fatigue generating component 306, efficiency generating component 308 and GUI 310 may be combined as a unitary device.

Further, in some embodiments, at least one of communication component 302, memory 304, fatigue generating component 306, efficiency generating component 308 and GUI 310 may be implemented as a processor working in conjunction with a tangible processor-readable media for carrying or having processor-executable instructions or data structures stored thereon.

Communication component 302 receives detected signals from sensors 204, 208, and 212 via communication channels 216, 218, and 220, and provides the detected signals to memory 304 via communication channel 312.

Memory 304 may any known type of memory, non-limiting examples of which include a random access memory (RAM) a hard drive, a flash memory, a rewritable optical disk, a rewritable magnetic tape, any suitable volatile/non-volatile computer readable storage medium, or any combination thereof. Memory 304 can store the detected signals and can provide the detected signals to fatigue generating component 306 via communication channel 314 or to efficiency generating component 308 via communication channel 316.

Fatigue generating component 306 receives detected signals from memory 304, generates a fatigue signal based on the detected signals, and provides the fatigue signal to GUI 310 via communication channel 318.

Efficiency generating component 308 receives detected signals from memory 304 via communication channel 314, generates an efficiency signal based on the detected signals, and provides the efficiency signal to GUI 310 via communication channel 320.

GUI 310 may encompass one or more input devices, software modules executing in conjunction with one or more operating systems and/or input devices, or any other such similar or related device, accessory, apparatus, and/or software application or module that enables or facilitates input and/or interaction with controller 214. GUI 310 receives the fatigue signal from fatigue generating component 306 via communication channel 318 and the efficiency signal from efficiency generating component 308 via communication channel 320, and provides the fatigue signal and efficiency signal to the user.

Communication channels 312, 314, 316, 318 and 320 may be any known type of wired or wireless communication channel that enables communication between two devices.

Figure 4:
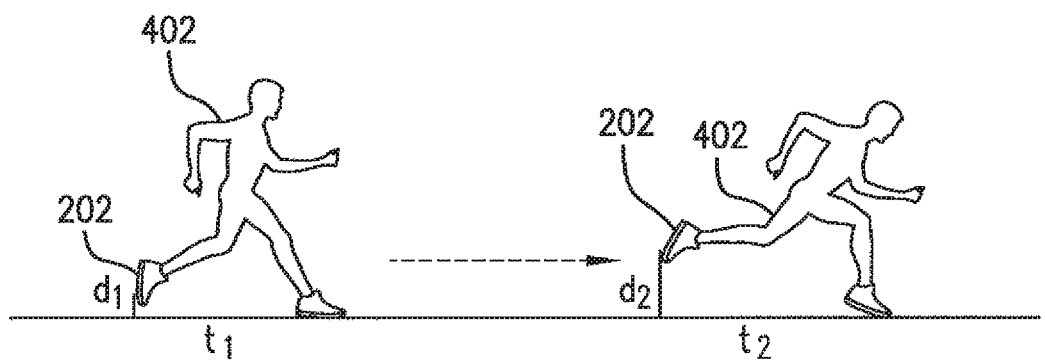
FIG. 4 illustrates a method of determining cadence and loft with a first sensor in accordance with aspects of the present invention.

FIG. 4 illustrates an example method of determining cadence and loft with a first sensor in accordance with aspects of the present invention. As shown in the figure, runner 402 is wearing shoes 202. Runner 402 is shown running at two different times, $t_1$ and $t_2$. At time $t_1$, the loft of shoe 202 is a distance $d_1$ from the ground, and at time $t_2$ the loft of shoe 202 is distance $d_2$ from the ground.

Figure 5:
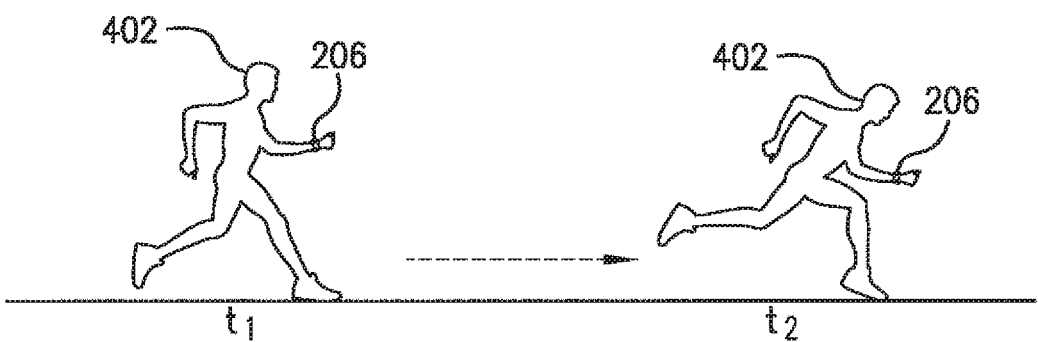
FIG. 5 illustrates a method of determining heart rate with a second sensor in accordance with aspects of the present invention.

FIG. 5 illustrates an example method of determining heart rate with a second sensor in accordance with aspects of the present invention. As shown in the figure, runner 402 is wearing smartwatch 206. Runner 402 is shown running at times, $t_1$ and $t_2$. At time t1, runner 402 has a first heartrate and at $t_2$, runner 402 has a second heartrate.

Figure 6:
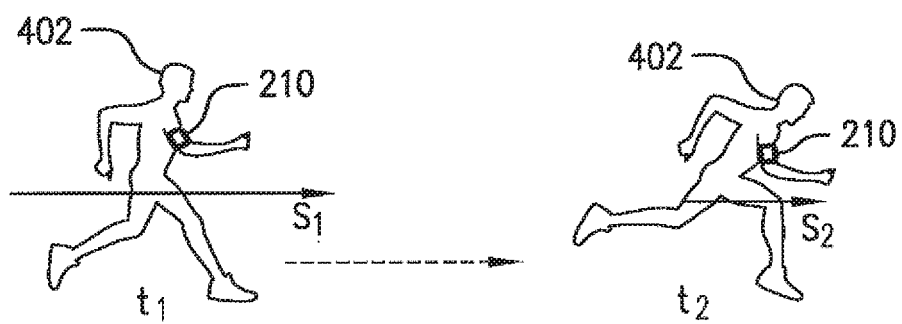
FIG. 6 illustrates a method of determining speed with a third sensor in accordance with aspects of the present invention.

FIG. 6 illustrates an example method of determining speed with a third sensor in accordance with aspects of the present invention. As shown in the figure, runner 402 is running with smartphone 212 attached to his arm. Runner 402 is shown running at times, $t_1$ and $t_2$. At time $t_1$, runner 402 is running at a speed $s_1$, and at time $t_2$, runner 402 is running at a speed $s_2$.

Figure 7:
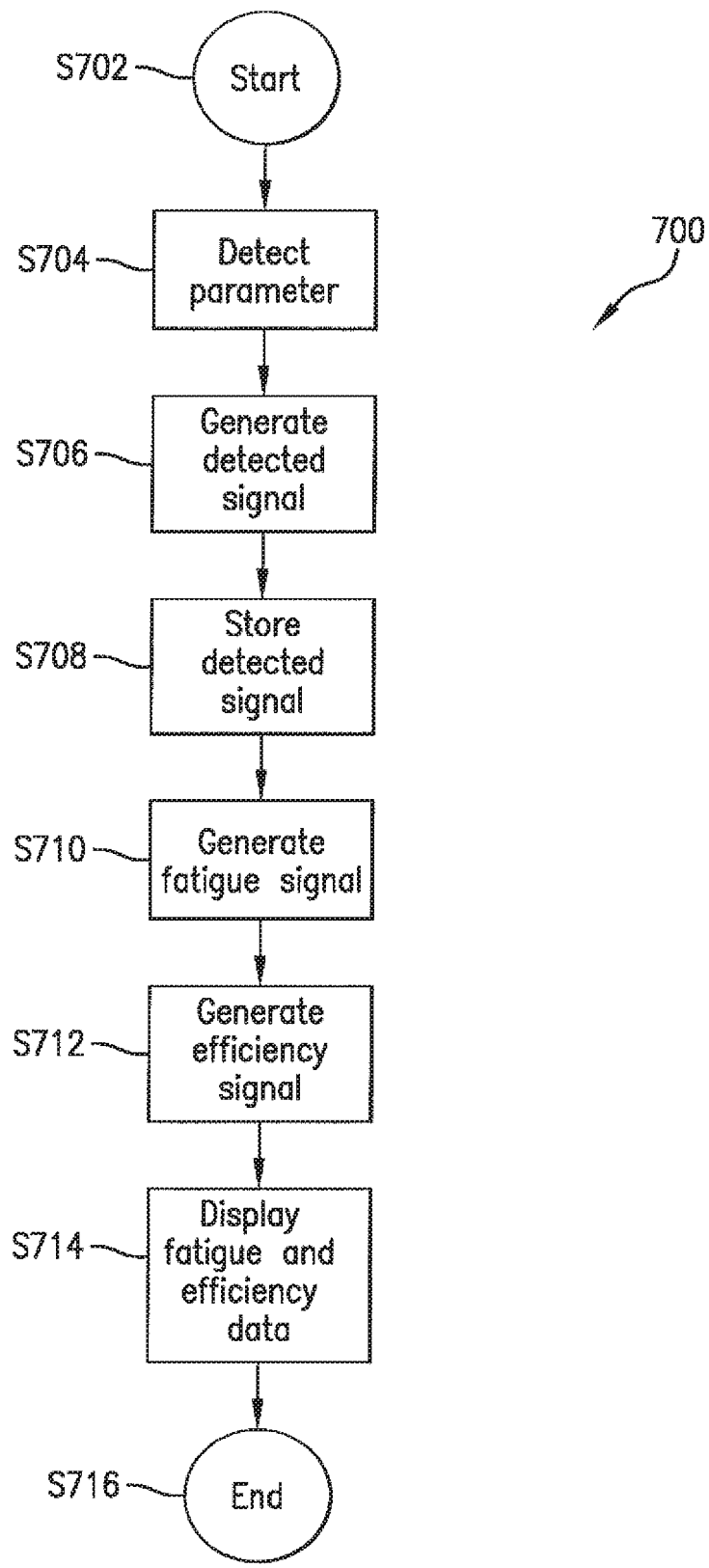
FIG. 7 illustrates a process by which input parameters are converted to fatigue and efficiency data in accordance with aspects of the present invention.

FIG. 7 illustrates an example method 700 in which input parameters are converted to fatigue and efficiency data in accordance with aspects of the present invention.

As shown in the figure, method 700 starts (S702) and parameters are detected (S704). For example, returning to FIG. 4, as runner 402 is running, sensor 204 (not shown) within shoes 202 can detect when each foot strikes the ground and is lifted from the ground. At time $t_1$, runner 402 may have just started running and is not very fatigued.

Suppose that for purposes of discussion, sensor 204 detects the cadence of runner 402 based on how quickly runner 402 lifts one foot off the ground and then places it back on the ground. In addition, sensor 204 detects the loft of shoes 202. At time $t_1$, the loft of shoes 202 is $d_1$. On the other hand, at time $t_2$, runner 402 may be more fatigued. When fatigue sets in, runner 402 has different cadence, which may be detected by sensor 204. For example, sensor 204 may detect a slower cadence, and may also detect a different loft, $d_2$, that may reflect a more fatigued runner.

In the above example, sensor 204 detects both the loft and cadence parameters. It is possible that sensor 204 may detect only one of those parameters, and another sensor would be included in shoes 202 to detect the other parameter.

Now, referring now to FIG. 5, suppose that as runner 402 is running, sensor 208 (not shown) within smartwatch 206 can detect the heartrate of runner 402 at different times. When fatigue sets in, runner 402 has different heartrate, which may be detected by sensor 208. Presume that the heartrate of runner 402 is rate $r_1$ at time $t_1$ but changes to rate $r_2$ at time $t_2$. As such, in this example, the change from heartrate $r_1$ to rate $r_2$ may indicate that runner 402 has become fatigued.

Referring now to FIG. 6, suppose that as runner 402 is running, sensor 212 (not shown) within smartphone 210 can detect the speed of runner 402 at different times. When fatigue sets in, runner 402 runs as a different speed, which may be detected by sensor 212. As a non-limiting example, the speed of runner 402 may be speed $s_1$ at time $t_1$ but it may slow down to speed $s_2$ at time $t_2$. As such, in this example, the change from speed $s_1$ to speed $s_2$ may indicate that runner 402 has become fatigued.

Returning to FIG. 7, now that the parameters have been detected (S704), detected signals are generated (S706).

Returning to FIG. 2, sensors 204, 208, and 212 generate detected signals based on the detected parameters. The signals contain data regarding instantaneous values of the detected parameters. In some example embodiments, the generated signals contain data regarding differences in instantaneous values of the detected parameters from $t_1$ to $t_2$. In some example embodiments, the generated signals contain data regarding instantaneous values of the detected parameters at time $t_1$ and at time $t_2$.

Sensors 204, 208, and 212 then send the detected signals to controller 214. As a non-limiting example, sensor 204 may generate detected signals based on the loft and cadence parameters and send the detected signals to controller 214 via communication channel 216. Sensor 208 may generate a detected signal based on the heartrate parameter and send the detected signal to controller 214 via communication channel 218. Sensor 212 may generate a detected signal based on the speed parameter and send the detected signal to controller 214 via communication channel 220.

Again, as mentioned previously, in this example embodiment, three sensors detect three parameters associated with an activity of a user. However, any number of sensors may be used to detect any number of parameters associated with an activity of a user.

Returning to FIG. 7, after the detected signals are generated (S706), the detected signals are stored (S708).

Referring to FIG. 3, communication component 302 receives the detected signals via communication channels 216, 218, and 220 and sends the detected signals to memory 304 via communication channel 312. Memory 304 stores the data of the detected signals.

In some embodiments the data of the signals are the signals themselves. For example, the data associated with the heartrate of the user may be digital signal from heartrate sensor 208, wherein one of the pulse number, the pulse amplitude, or pulse width indicates the heartrate of the user. As such, the actual signal may be stored as the data. In other embodiments, memory 304 may extract data from a signal. For example, memory 304 may extract a heartrate value of the user based on the received signal from sensor 208.

In some embodiments, the data of the detected signals are stored separately within memory 304. In some embodiments, the data of the detected signals are combined in some functional relationship so as to create a signature. Any known type of functional relationship may be used, non-limiting examples of which include addition, subtraction, multiplication, division, exponential and combinations thereof.

Returning to FIG. 7, after the data of the detected signals are stored (S708), a fatigue signal is generated (S710).

Referring to FIG. 3, fatigue generating component 306 retrieves the data of the detected signals from memory 304.

In some example embodiments, fatigue generating component 306 compares the data of each detected parameter with corresponding predetermined parameter thresholds to determine the fatigue level of runner 102. For example, fatigue generating component 306 compares the cadence data of runner 102, as detected by sensor 204, with an a priori cadence threshold, compares the heartrate data of runner, as detected by sensor 208, with an a priori heartrate threshold, and compares the speed data of runner 102, as detected by sensor 212, with an a priori speed threshold. In this manner, if any one of the detected parameters falls below the predetermined thresholds, it may be determined that runner 102 is fatigued. In such a case, a fatigue signal may merely be an indication that runner 102 is fatigued.

Further, in some embodiments, fatigue generating component 306 may compare the data of each detected parameter with corresponding predetermined parameter thresholds to determine the fatigue level of runner 102, and generate a fatigue value. For example, suppose that fatigue generating component 306 determines that the cadence data of runner 102, as detected by sensor 204, 5% greater than the a priori cadence threshold. This 5% increase over the a priori cadence threshold may be associated with a predetermined amount of fatigue. In some embodiment, the results of such comparisons of all detected parameters may be used to generate an associated predetermine amount of fatigue. In such a case, a fatigue signal may be a value indicating an amount of fatigue of runner 102.

In some embodiments, fatigue generating component 306 generates a fatigue signal at predetermined times, e.g., at predetermined time intervals. In some embodiments, fatigue generating component 306 generates a fatigue signal the end of an activity. In some embodiments, fatigue generating component 306 generates a fatigue signal as instructed by runner 102, for example via GUI 310.

Consider the situation wherein as fatigue increases, cadence, loft, and speed generally decrease as heartrate generally increases. In such a case, fatigue generating component 306 determines, based on the change in the detected signals over time, the fatigue of the runner at a given point in time. Fatigue generating component 306 may generate a fatigue signal based on how fatigued the runner is at a given point in time.

In general, a runner's fatigue level is inversely proportional to the runner's efficiency level, so the fatigue signal generated by fatigue generating component 306 will be inversely related to the efficiency signal generated by efficiency generating component 308. The fatigue signal is then sent to GUI 310.

In some embodiments, fatigue generating component 306 may generate fatigue signals instantaneously during a run, notifying the runner of his fatigue level while running. Fatigue generating component 306 may also generate fatigue signals after one or more runs to notify the runner how his fatigue levels change over time.

Referring to FIG. 7, after the fatigue signal is generated (S710), the efficiency signal is generated (S712).

In some example embodiments, efficiency generating component 308 compares the data of each detected parameter with corresponding predetermined parameter thresholds to determine the efficiency level of runner 102. For example, efficiency generating component 308 compares the cadence data of runner 102, as detected by sensor 204, with an efficient a priori cadence threshold, compares the heartrate data of runner, as detected by sensor 208, with an efficient a priori heartrate threshold, and compares the speed data of runner 102, as detected by sensor 212, with an efficient a priori speed threshold. In this manner, if any one of the detected parameters falls below the predetermined efficient thresholds, it may be determined how efficient runner 102 is running. In such a case, a fatigue signal may merely be an indication that runner 102 is running efficiently.

Further, in some embodiments, efficiency generating component 308 may compare the data of each detected parameter with corresponding predetermined parameter thresholds to determine the level of runner 102, and generate an efficiency value. For example, suppose that efficiency generating component 308 determines that the cadence data of runner 102, as detected by sensor 204, is 5% greater than the efficient a priori cadence threshold. This 5% increase over the efficient a priori cadence threshold may be associated with a predetermined efficiency amount. In some embodiments, the results of such comparisons of all detected parameters may be used to generate an associated predetermined efficiency amount. In such a case, an efficiency signal may be a value indicating an efficiency amount of runner 102.

In some embodiments, efficiency generating component 306 generates an efficiency signal at predetermined times, e.g., at predetermined time intervals. In some embodiments, efficiency generating component 306 generates an efficiency signal the end of an activity. In some embodiments, efficiency generating component 306 generates an efficiency signal as instructed by runner 102, for example via GUI 310.

In general, a runner's efficiency level is inversely proportional to the runner's fatigue level, so the efficiency signal generated by efficiency generating component 308 will be inversely related to the fatigue signal generated by fatigue generating component 306. The efficiency signal is then sent to GUI 310.

Efficiency generating component 308 may generate efficiency signals instantaneously during a run, notifying the runner of his efficiency level while running. Efficiency generating component 308 may also generate efficiency signals after one or more runs to notify the runner how his efficiency levels change over time.

It should be noted that in the example discussed above, the fatigue signal is generated (S710) prior to the efficiency signal being generated (S712). It should be noted that in some embodiments, the efficiency signal is generated prior to the fatigue signal being generated. Further, in some embodiments, the fatigue signal is generated concurrently with the efficiency signal.

Returning to FIG. 7, after the efficiency signal is generated (S712), the fatigue and efficiency data is displayed (S714).

Referring to FIG. 3, the runner may want to view his efficiency and fatigue data, either during a run or after a run. In some embodiments, to view the data during a run, the runner may send a request to view the data to GUI 310 via communication channel 222. As a non-limiting example, and with reference to FIG. 5, runner 402 may enter his preference to view his fatigue and efficiency data via smartwatch 206. Returning to FIG. 3. GUI 310 would then send the request to fatigue generating component 306 and efficiency generating component 308, and each of those components would provide the appropriate, real time data to GUI 310. The runner would then be able to view the real time fatigue and efficiency data via GUI 310.

In another embodiment, the runner may want to view his fatigue and efficiency data after a run is complete in order to compare his fatigue and efficiency data over time. As a non-limiting example, the runner may connect all of his devices with sensors to a laptop computer, and he may enter his preference to view his fatigue and efficiency data via the laptop computer. GUI 310 would then send the request to fatigue generating component 306 and efficiency generating component 308, and each of the components would communicate with memory 304 to provide the data the runner desires. For example, the runner may desire to view his fatigue and efficiency data for all runs over the past two weeks. GUI 310 would then display the data to the runner, who could analyze his performance over time and make modifications to his training regimen as desired.

Returning to FIG. 7, after the fatigue and efficiency data is displayed (S714), method 700 ends (S716).

Some conventional smart wearable devices may detect a parameter of a runner to determine how efficient a runner is running. However, any one device may be limited in its accuracy in determining efficiency.

In accordance with aspects of the present invention, a plurality of smart devices detect a plurality of parameters associated with an activity of a user. These plural detected parameters are used to provide a more accurate measurement of a user's activity efficiency. Further, these plural detected parameters are used to provide an accurate measurement of a user's fatigue during the activity.

The foregoing description of various preferred embodiments have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A device for use by a user, the device comprising:
   a receiver apparatus configured to:
      receive a first signal comprising a measure of one or more exercise parameters of the user at a first time period of an exercise session, the first signal being received from one or more sensors;
      receive a second signal comprising a measure of the one or more exercise parameters of the user at a second time period of the exercise session, the second time period different from the first time period, the second signal being received from the one or more sensors; and
   a processor configured to:
      store the first and second signals in a memory associated to the processor;
      generate a fatigue signal based on a comparison of the measured one or more exercise parameters of the first signal to the respective measured one or more exercise parameters of the second signal;
      generate an exercise efficiency signal based on a comparison of the measured one or more exercise parameters of the second signal to an a priori exercise parameter threshold; and
      cause the exercise efficiency signal and the fatigue signal to be simultaneously displayed on a display device.

2. The device of claim 1, wherein the fatigue signal is inversely related to the exercise efficiency signal.

3. The device of claim 1,
   wherein the one or more sensors from which the first signal is received are configured to detect the cadence of the user at the first time;
   wherein the one or more sensors from which the second signal is received are configured to detect the cadence of the user at the second time; and
   wherein the fatigue signal is based on a change in cadence of the user from the first time to the second time.

4. The device of claim 1,
   wherein the one or more sensors from which the first signal is received are configured to detect the loft of the first foot of the user at the first time;
   wherein the one or more sensors from which the second signal is received are configured to detect the loft of the first foot of the user at the second time; and
   wherein the fatigue signal is based on a change in the loft of the first food of the user from the first time to the second time.

5. The device of claim 1, wherein the efficiency signal is based on a comparison of the measured one or more exercise parameters of the first signal to a predetermined threshold therefor and/or a comparison of the one or more exercise parameters of the second signal to a predetermined threshold therefor.

6. The device of claim 5, wherein the fatigue signal is based on a comparison of the measured one or more exercise parameters of the first signal to a predetermined threshold therefor and/or a comparison of the one or more exercise parameters of the second signal to a predetermined threshold therefor.

7. The device of claim 1,
   wherein the one or more exercise parameters of the user at the first time period includes at least one of: a heartrate of the user, a cadence of the user, a speed of the user, and a loft of a first foot of the user; and
   wherein the one or more exercise parameters of the user at the second time period includes at least one of: the heartrate of the user, the cadence of the user, a speed of the user, and a loft of a first foot of the user.

8. The method of claim 1, wherein the one or more sensors include a sensor mounted in a shoe.

9. A method comprising:
   receiving a first detected signal based on a first parameter detected at a first time, the first parameter comprising at least one of: a heartrate of the user, a cadence of the user, a speed of the user, and a loft of a foot of the user;

receiving a second detected signal based on a second parameter detected at a second time, the second parameter either (i) a different parameter than the first parameter and comprising at least one of: the heartrate of the user, the cadence of the user, the speed of the user, and the loft of the foot of the user, wherein the second parameter is detected at the first time, or (ii) a same parameter as the first parameter; and generating, via an efficiency generating component, an efficiency signal;

wherein, when the second parameter is a same parameter as the first parameter, the efficiency signal is generated based on a comparison of the first detected signal to the second detected signal; and wherein, when the second detected parameter is a different parameter than the first parameter, the efficiency signal is generated based on a comparison of the first detected signal and the second detected signal to respective predetermined thresholds therefor.

10. The method of claim 9, further comprising generating, via a fatigue generating component, a fatigue signal, and causing a fatigue signal and the efficiency signal to be simultaneously displayed on a display device.

11. The method of claim 9,
wherein the act of detecting a first parameter comprises detecting the first parameter as the cadence of the user at the first time;
wherein the act of detecting a second parameter comprises detecting the second parameter as the cadence of the user at the second time; and
wherein the act of generating the efficiency signal comprises generating the efficiency signal based on a change in cadence of the user.

12. The method of claim 9,
wherein the act of detecting the first parameter comprises detecting the first parameter as the loft of the first foot of the user at the first time;
wherein the act of detecting the second parameter comprises detecting the second parameter as the loft of the first foot of the user at the second time; and
wherein the act of generating the efficiency signal comprises generating the efficiency signal based on a change in loft of the user.

13. The method of claim 9, wherein when the first detected parameter and the second detected parameter comprise a same one or more of: the heartrate of the user, the cadence of the user, the speed of the user, the loft of the foot of the user, the fatigue signal being generated based on a comparison of the first detected signal to the second detected signal.

14. The method of claim 9, wherein when the first detected parameter and the second detected parameter comprise different ones of: the heartrate of the user at the first time, the cadence of the user at the first time, the speed of the user at the first time, the loft of the first foot of the user at the first time, the fatigue signal being generated based on a comparison of the first detected signal and the second detected signal to respective predetermined thresholds therefor.

15. The method of claim 9, further comprising causing at least one of the efficiency signal and the fatigue signal to be displayed at a display device.

16. A non-transitory, tangible, computer-readable media having computer-readable instructions stored thereon, the computer-readable instructions being capable of being read by a computer and being capable of instructing the computer to:

receive a first sensed parameter of the user at a first time, the first sensed parameter selected from a first group of parameters for the user;

receive a second sensed parameter of the user at a second time, the second sensed parameter comprising at least (i) a different one of the first group or (ii) at least one of a second group;

generate an efficiency signal;

generate a fatigue signal; and display at least one of the efficiency signal and the fatigue signal;

wherein, when the second sensed parameter comprises a member of the second group, the generation of the efficiency signal and/or the fatigue signal comprises a comparison of the first sensed parameter to the second sensed parameter; and wherein, when the second sensed parameter comprises a member of the first group, the generation of the efficiency signal and/or the fatigue signal comprises a comparison of each of the first and second sensed parameters to respective thresholds therefor.

17. The non-transitory, tangible, computer-readable media of claim 16,
wherein the first group comprises: the heartrate of the user at the first time, the cadence of the user at the first time, the speed of the user at the first time, the loft of the first foot of the user at the first time;
wherein the second group comprises: a heartrate of the user at a second time, a cadence of the user at the second time, a speed of the user at the second time, and a loft of the first foot of the user at the second time.

18. The non-transitory, tangible, computer-readable media of claim 16, wherein the generation of the fatigue signal comprises generation thereof so as to be inversely related to the efficiency signal.

19. The non-transitory, tangible, computer-readable media of claim 16,
wherein the first sensed parameter comprises the cadence of the user at the first time;
wherein the second sensed parameter comprises the cadence of the user at the second time; and
wherein the efficiency signal comprises a measure of a change in cadence of the user from the first time to the second time.

20. The non-transitory, tangible, computer-readable media of claim 16, wherein the computer-readable instructions are capable of instructing the computer to perform the method
wherein the first sensed parameter comprises the loft of the first foot of the user at the first time;
wherein the second sensed parameter comprises the loft of the first foot of the user at the second time; and
wherein the efficiency signal comprises a measure of a change in loft of the first foot of the user from the first time to the second time.

21. The non-transitory, tangible, computer-readable media of claim 16, wherein the generation of the exercise efficiency signal is based on a comparison of a measured exercise parameter of the second sensed parameter to an a priori exercise parameter threshold.

* * * * *